United States Patent
Godlewski et al.

(10) Patent No.: US 9,422,222 B2
(45) Date of Patent: *Aug. 23, 2016

(54) PROCESS FOR PRODUCTION OF ACRYLIC ACID OR ITS DERIVATIVES FROM HYDROXYPROPIONIC ACID OR ITS DERIVATIVES

(71) Applicant: The Procter & Gamble Company, Cincinnati, OH (US)

(72) Inventors: Jane Ellen Godlewski, Loveland, OH (US); Janette Villalobos, Cincinnati, OH (US); Dimitris Ioannis Collias, Mason, OH (US); Juan Estaban Velasquez, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/511,192

(22) Filed: Oct. 10, 2014

(65) Prior Publication Data

US 2015/0031912 A1   Jan. 29, 2015

Related U.S. Application Data

(62) Division of application No. 13/760,483, filed on Feb. 6, 2013, now Pat. No. 8,884,050.

(60) Provisional application No. 61/623,054, filed on Apr. 11, 2012.

(51) Int. Cl.
| | | |
|---|---|---|
| C07C 51/377 | (2006.01) | |
| C07C 51/48 | (2006.01) | |
| B01J 27/18 | (2006.01) | |
| B01J 27/187 | (2006.01) | |
| B01J 27/25 | (2006.01) | |
| C07C 51/09 | (2006.01) | |
| C07C 57/04 | (2006.01) | |
| A61F 13/534 | (2006.01) | |
| C08F 2/10 | (2006.01) | |
| B01J 27/16 | (2006.01) | |
| B01J 27/185 | (2006.01) | |
| B01J 27/186 | (2006.01) | |
| B01J 27/188 | (2006.01) | |
| B01J 27/195 | (2006.01) | |
| B01J 27/198 | (2006.01) | |
| B01J 35/02 | (2006.01) | |
| B01J 37/00 | (2006.01) | |
| B01J 37/04 | (2006.01) | |
| B01J 37/08 | (2006.01) | |
| C07C 51/44 | (2006.01) | |

(52) U.S. Cl.
CPC ............ *C07C 51/48* (2013.01); *A61F 13/534* (2013.01); *B01J 27/16* (2013.01); *B01J 27/1806* (2013.01); *B01J 27/186* (2013.01); *B01J 27/187* (2013.01); *B01J 27/188* (2013.01); *B01J 27/1811* (2013.01); *B01J 27/1817* (2013.01); *B01J 27/1853* (2013.01); *B01J 27/1856* (2013.01); *B01J 27/195* (2013.01); *B01J 27/198* (2013.01); *B01J 27/25* (2013.01); *B01J 35/023* (2013.01); *B01J 37/0036* (2013.01); *B01J 37/04* (2013.01); *B01J 37/08* (2013.01); *C07C 51/09* (2013.01); *C07C 51/377* (2013.01); *C07C 51/44* (2013.01); *C07C 57/04* (2013.01); *C08F 2/10* (2013.01)

(58) Field of Classification Search
None
See application file for complete search history.

(56) References Cited

U.S. PATENT DOCUMENTS

| | | |
|---|---|---|
| 3,781,222 A | 12/1973 | Weisang et al. |
| 4,695,661 A | 9/1987 | Homann et al. |
| 4,786,756 A | 11/1988 | Paparizos et al. |
| 7,683,220 B2 | 3/2010 | Matsunami et al. |

FOREIGN PATENT DOCUMENTS

| | | |
|---|---|---|
| CN | 200910054519.7 | 7/2009 |
| GB | 1489832 | 10/1977 |
| WO | WO 03/082795 A2 | 10/2003 |

OTHER PUBLICATIONS

Gunter et al.; J. Catalysis 148:252-260, 1994.
Hong et al.; Appl. Catal. A: General 396:194-200, 2011.
Kirk-Othmer Encylcopedia of Chemical Technology, vol. 1, pp. 324-369, 5th Ed., John Wiley & Sons, Inc., 2004.
Tam et al.; Ind. Eng. Chem. Res: 38:3873-3877, 1999.

Primary Examiner — Karl J Puttlitz
(74) Attorney, Agent, or Firm — Brent M. Peebles

(57) ABSTRACT

Processes for the catalytic dehydration of hydroxypropionic acid, hydroxypropionic acid derivatives, or mixtures thereof to acrylic acid, acrylic acid derivatives, or mixtures thereof with high yield and selectivity and without significant conversion to undesired side products, such as, acetaldehyde, propanoic acid, and acetic acid, are provided.

35 Claims, No Drawings

PROCESS FOR PRODUCTION OF ACRYLIC ACID OR ITS DERIVATIVES FROM HYDROXYPROPIONIC ACID OR ITS DERIVATIVES

FIELD OF THE INVENTION

The present invention generally relates to processes that catalytically convert hydroxypropionic acid, hydroxypropionic acid derivatives, or mixtures thereof to acrylic acid, acrylic acid derivatives, or mixtures thereof. More specifically, the invention relates to processes useful for the dehydration of hydroxypropionic acid, hydroxypropionic acid derivatives, or mixtures thereof to acrylic acid, acrylic acid derivatives, or mixtures thereof with high yield and selectivity to acrylic acid, acrylic acid derivatives, or mixtures thereof, short residence time, and without significant conversion of the hydroxypropionic acid, hydroxypropionic acid derivatives, or mixtures thereof to undesired side products, such as, for example, acetaldehyde, propanoic acid, acetic acid, 2,3-pentanedione, carbon dioxide, and carbon monoxide.

BACKGROUND OF THE INVENTION

Acrylic acid, acrylic acid derivatives, or mixtures thereof have a variety of industrial uses, typically consumed in the form of polymers. In turn, these polymers are commonly used in the manufacture of, among other things, adhesives, binders, coatings, paints, polishes, detergents, flocculants, dispersants, thixotropic agents, sequestrants, and superabsorbent polymers, which are used in disposable absorbent articles, including diapers and hygienic products, for example. Acrylic acid is commonly made from petroleum sources. For example, acrylic acid has long been prepared by catalytic oxidation of propylene. These and other methods of making acrylic acid from petroleum sources are described in the Kirk-Othmer Encyclopedia of Chemical Technology, Vol. 1, pgs. 342-369 ($5^{th}$ Ed., John Wiley & Sons, Inc., 2004). Petroleum-based acrylic acid contributes to greenhouse emissions due to its high petroleum derived carbon content. Furthermore, petroleum is a non-renewable material, as it takes hundreds of thousands of years to form naturally and only a short time to consume. As petrochemical resources become increasingly scarce, more expensive, and subject to regulations for $CO_2$ emissions, there exists a growing need for bio-based acrylic acid, acrylic acid derivatives, or mixtures thereof that can serve as an alternative to petroleum-based acrylic acid, acrylic acid derivatives, or mixtures thereof.

Many attempts have been made over the last 40 to 50 years to make bio-based acrylic acid, acrylic acid derivatives, or mixtures thereof from non-petroleum sources, such as lactic acid (also known as 2-hydroxypropionic acid), 3-hydroxypropionic acid, glycerin, carbon monoxide and ethylene oxide, carbon dioxide and ethylene, and crotonic acid. From these non-petroleum sources, only lactic acid is produced today in high yield from sugar ($\geq 90\%$ of theoretical yield, or equivalently, $\geq 0.9$ g of lactic acid per g of sugar) and purity, and economics which could support producing acrylic acid cost competitively to petroleum-based acrylic acid. As such, lactic acid or lactate presents a real opportunity of serving as feedstock for bio-based acrylic acid, acrylic acid derivatives, or mixtures thereof. Also, 3-hydroxypropionic acid is expected to be produced at commercial scale in a few years, and as such, 3-hydropropionic acid will present another real opportunity of serving as feedstock for bio-based acrylic acid, acrylic acid derivatives, or mixtures thereof. Sulfate salts; phosphate salts; mixtures of sulfate and phosphate salts; bases; zeolites or modified zeolites; metal oxides or modified metal oxides; and supercritical water are the main catalysts which have been used to dehydrate lactic acid or lactate to acrylic acid, acrylic acid derivatives, or mixtures thereof in the past with varying success.

For example, in U.S. Pat. No. 4,786,756 (issued in 1988), the inventors claim the vapor phase dehydration of lactic acid or ammonium lactate to acrylic acid using aluminum phosphate ($AlPO_4$) treated with an aqueous inorganic base as a catalyst. As examples, the '756 patent discloses a maximum yield of acrylic acid of 43.3% when lactic acid was fed into the reactor at approximately atmospheric pressure, and a respective yield of 61.1% when ammonium lactate was fed into the reactor. In both examples, acetaldehyde was produced at yields of 34.7% and 11.9%, respectively, and other side products were also present in large quantities, such as, propionic acid, CO, and $CO_2$. Omission of the base treatment caused increased amounts of the side products. Another example is Hong et al. (2011) *Appl. Catal. A: General* 396:194-200, who developed and tested composite catalysts made with $Ca_3(PO_4)_2$ and $Ca_2(P_2O_7)$ salts with a slurry-mixing method. The catalyst with the highest yield of acrylic acid from methyl lactate was the 50%-50% (by weight) catalyst. It yielded 68% acrylic acid, about 5% methyl acrylate, and about 14% acetaldehyde at 390° C. The same catalyst achieved 54% yield of acrylic acid, 14% yield of acetaldehyde, and 14% yield of propionic acid from lactic acid.

Prof. D. Miller's group at Michigan State University (MSU) published many papers on the dehydration of lactic acid or lactic acid esters to acrylic acid and 2,3-pentanedione, such as, Gunter et al. (1994) *J. Catalysis* 148: 252-260; and Tam et al. (1999) *Ind. Eng. Chem. Res.* 38:3873-3877. The best acrylic acid yields reported by the group were about 33% when lactic acid was dehydrated at 350° C. over low surface area and pore volume silica impregnated with NaOH. In the same experiment, the acetaldehyde yield was 14.7% and the propionic acid yield was 4.1%. Examples of other catalysts tested by the group were $Na_2SO_4$, NaCl, $Na_3PO_4$, $NaNO_3$, $Na_2SiO_3$, $Na_4P_2O_7$, $NaH_2PO_4$, $Na_2HPO_4$, $Na_2HAsO_4$, $NaC_3H_5O_3$, NaOH, CsCl, $Cs_2SO_4$, KOH, CsOH, and LiOH. In all cases, the above referenced catalysts were tested as individual components, not in mixtures. Finally, the group suggested that the yield to acrylic acid is improved and the yield to the side products is suppressed when the surface area of the silica support is low, reaction temperature is high, reaction pressure is low, and residence time of the reactants in the catalyst bed is short.

Finally, the Chinese patent application 200910054519.7 discloses the use of ZSM-5 molecular sieves modified with aqueous alkali (such as, $NH_3$, NaOH, and $Na_2CO_3$) or a phosphoric acid salt (such as, $NaH_2PO_4$, $Na_2HPO_4$, $LiH_2PO_4$, $LaPO_4$, etc.). The best yield of acrylic acid achieved in the dehydration of lactic acid was 83.9%, however that yield came at very long residence times.

Therefore, the manufacture of acrylic acid, acrylic acid derivatives, or mixtures thereof from lactic acid or lactate by processes, such as those described in the literature noted above, leads to: 1) yields of acrylic acid, acrylic acid derivatives, or mixtures thereof not exceeding 70%; 2) low selectivities of acrylic acid, acrylic acid derivatives, or mixtures thereof, i.e., significant amounts of undesired side products, such as, acetaldehyde, 2,3-pentanedione, propionic acid, CO, and $CO_2$; 3) long residence times in the catalyst beds; and 4) catalyst deactivation in short time on stream (TOS). The side products can deposit onto the catalyst resulting in fouling, and premature and rapid deactivation of the catalyst. Further, once deposited, these side products can catalyze other undesired reactions, such as polymerization reactions. Aside from depositing on the catalysts, these side products, even when present in only small amounts, impose additional costs in processing acrylic acid (when present in the reaction product effluent) in the manufacture of superabsorbent polymers (SAP), for example. These deficiencies of the prior art processes and catalysts render them commercially non-viable.

Accordingly, there is a need for processes for the dehydration of hydroxypropionic acid, hydroxypropionic acid derivatives, or mixtures thereof to acrylic acid, acrylic acid derivatives, or mixtures thereof, with high yield, selectivity, and efficiency (i.e., short residence time), and high longevity catalysts.

SUMMARY OF THE INVENTION

In one embodiment of the present invention, a process for converting hydroxypropionic acid, hydroxypropionic acid derivatives, or mixtures thereof to acrylic acid, acrylic acid derivatives, or mixtures thereof is provided comprising the following steps:
  a) Providing an aqueous solution comprising hydroxypropionic acid, hydroxypropionic acid derivatives, or mixtures thereof, wherein said hydroxypropionic acid is in monomeric form in said aqueous solution;
  b) Combining said aqueous solution with an inert gas to form an aqueous solution/gas blend;
  c) Evaporating said aqueous solution/gas blend to produce a gaseous mixture; and
  d) Dehydrating said gaseous mixture by contacting said gaseous mixture with a dehydration catalyst under a pressure of at least about 80 psig, producing said acrylic acid, acrylic acid derivatives, or mixtures thereof.

In another embodiment of the present invention, a process for converting hydroxypropionic acid, hydroxypropionic acid derivatives, or mixtures thereof to acrylic acid, acrylic acid derivatives, or mixtures thereof is provided comprising the following steps:
  a) Providing an aqueous solution comprising hydroxypropionic acid, hydroxypropionic acid derivatives, or mixtures thereof, wherein said hydroxypropionic acid comprises oligomers in said aqueous solution;
  b) Heating said aqueous solution at a temperature from about 50° C. to about 100° C. to remove said oligomers of said hydroxypropionic acid and produce an aqueous solution of monomeric hydroxypropionic acid;
  c) Combining said aqueous solution of monomeric hydroxypropionic acid with an inert gas to form an aqueous solution/gas blend;
  d) Evaporating said aqueous solution/gas blend to produce a gaseous mixture; and
  e) Dehydrating said gaseous mixture by contacting said mixture with a dehydration catalyst, producing said acrylic acid, acrylic acid derivatives and mixtures thereof.

In yet another embodiment of the present invention, a process for converting hydroxypropionic acid, hydroxypropionic acid derivatives, or mixtures thereof to acrylic acid, acrylic acid derivatives, or mixtures thereof is provided comprising the following steps:
  a) Providing an aqueous solution comprising hydroxypropionic acid, hydroxypropionic acid derivatives, or mixtures thereof, wherein said hydroxypropionic acid is in monomeric form in said aqueous solution;
  b) Combining said aqueous solution with an inert gas to form an aqueous solution/gas blend;
  c) Evaporating said aqueous solution/gas blend to produce a gaseous mixture;
  d) Dehydrating said gaseous mixture by contacting said mixture with a dehydration catalyst, producing said acrylic acid, acrylic acid derivatives, or mixtures thereof; and
  e) Cooling said acrylic acid, acrylic acid derivatives, or mixtures thereof at a GHSV of more than about 360 $h^{-1}$.

In one embodiment of the present invention, a process for converting lactic acid to acrylic acid is provided comprising the following steps:
  a) Diluting an about 88% lactic acid aqueous solution with water to form an about 20 wt % lactic acid aqueous solution;
  b) Heating said about 20 wt % lactic acid aqueous solution at a temperature from about 95° C. to about 100° C. to remove oligomers of said lactic acid, producing a monomeric lactic acid aqueous solution comprising at least 95 wt % of said lactic acid in monomeric form based on the total amount of lactic acid;
  c) Combining said monomeric lactic acid aqueous solution with nitrogen to form an aqueous solution/gas blend;
  d) Evaporating said aqueous solution/gas blend in a reactor with inside surface of borosilicate glass at a GHSV of about 7,200 $h^{-1}$ at a temperature from about 300° C. to about 350° C. to produce a gaseous mixture comprising about 2.5 mol % lactic acid and about 50 mol % water;
  e) Dehydrating said gaseous mixture in a reactor with inside surface of borosilicate glass at a GHSV of about 3,600 $h^{-1}$ at a temperature from about 350° C. to about 425° C. by contacting said mixture with a dehydration catalyst under a pressure of about 360 psig, producing said acrylic acid; and
  f) Cooling said acrylic acid to give an acrylic acid solution at a GHSV from about 360 $h^{-1}$ to about 36,000 $h^{-1}$.

In another embodiment of the present invention, a process for converting hydroxypropionic acid, derivatives of hydroxypropionic acid, and mixtures thereof to acrylic acid, acrylic acid derivatives, or mixtures thereof is provided comprising the following steps:
  a) Providing an aqueous solution comprising hydroxypropionic acid, hydroxypropionic acid derivatives, or mixtures thereof, wherein said hydroxypropionic acid is in monomeric form in said aqueous solution, and wherein the hydroxypropionic acid, hydroxypropionic acid derivatives, or mixtures thereof comprise from about 10 wt % to about 25 wt % of said aqueous solution;
  b) Combining said aqueous solution with an inert gas to form an aqueous solution/gas blend;
  c) Evaporating said aqueous solution/gas blend to produce a gaseous mixture; and
  d) Dehydrating said gaseous mixture by contacting said mixture with a dehydration catalyst producing said acrylic acid, acrylic acid derivatives, or mixtures thereof.

In yet another embodiment of the present invention, a process for converting alkyl lactates to acrylic acid, acrylic acid derivatives, or mixtures thereof is provided comprising the following steps:
 a) Providing alkyl lactates or a solution comprising alkyl lactates and a solvent;
 b) Combining said alkyl lactates or said solution comprising said alkyl lactates and said solvent with an inert gas to form a liquid/gas blend;
 c) Evaporating said liquid/gas blend to produce a gaseous mixture; and
 d) Dehydrating said gaseous mixture by contacting said gaseous mixture with a dehydration catalyst under a pressure of at least about 80 psig, producing said acrylic acid, acrylic acid derivatives, or mixtures thereof.

Additional features of the invention may become apparent to those skilled in the art from a review of the following detailed description, taken in conjunction with the examples and the appended claims.

DETAILED DESCRIPTION OF THE INVENTION

I Definitions

As used herein, the term "condensed phosphate" refers to any salts containing one or several P—O—P bonds generated by corner sharing of $PO_4$ tetrahedra.

As used herein, the term "cyclophosphate" refers to any cyclic condensed phosphate constituted of two or more corner-sharing $PO_4$ tetrahedra.

As used herein, the term "monophosphate" or "orthophosphate" refers to any salt whose anionic entity, $[PO_4]^{3-}$, is composed of four oxygen atoms arranged in an almost regular tetrahedral array about a central phosphorus atom.

As used herein, the term "oligophosphate" refers to any polyphosphates that contain five or less $PO_4$ units.

As used herein, the term "polyphosphate" refers to any condensed phosphates containing linear P—O—P linkages by corner sharing of $PO_4$ tetrahedra leading to the formation of finite chains.

As used herein, the term "ultraphosphate" refers to any condensed phosphate where at least two $PO_4$ tetrahedra of the anionic entity share three of their corners with the adjacent ones.

As used herein, the term "cation" refers to any atom or group of covalently-bonded atoms having a positive charge.

As used herein, the term "monovalent cation" refers to any cation with a positive charge of +1.

As used herein, the term "polyvalent cation" refers to any cation with a positive charge equal or greater than +2.

As used herein, the term "anion" refers to any atom or group of covalently-bonded atoms having a negative charge.

As used herein, the term "heteropolyanion" refers to any anion with covalently bonded $XO_p$ and $YO_r$ polyhedra, and thus includes X—O—Y and possibly X—O—X and Y—O—Y bonds, wherein X and Y represent any atoms, and wherein p and r are any positive integers.

As used herein, the term "heteropolyphosphate" refers to any heteropolyanion, wherein X represents phosphorus (P) and Y represents any other atom.

As used herein, the term "phosphate adduct" refers to any compound with one or more phosphate anions and one or more non-phosphate anions that are not covalently linked.

As used herein, the terms "LA" refers to lactic acid, "AA" refers to acrylic acid, "AcH" refers to acetaldehyde, and "PA" refers to propionic acid.

As used herein, the term "particle span" refers to a statistical representation of a given particle sample and is equal to $(D_{v,0.90}-D_{v,0.10})/D_{v,0.50}$. The term "median particle size" or $D_{v,0.50}$ refers to the diameter of a particle below which 50% of the total volume of particles lies. Further, $D_{v,0.10}$ refers to the particle size that separates the particle sample at the 10% by volume fraction and $D_{v,0.90}$, is the particle size that separates the particle sample at the 90% by volume fraction.

As used herein, the term "conversion" in % is defined as [hydroxypropionic acid, hydroxypropionic acid derivatives, or mixtures thereof flow rate in (mol/min)–hydroxypropionic acid, hydroxypropionic acid derivatives, or mixtures thereof flow rate out (mol/min)]/[hydroxypropionic acid, hydroxypropionic acid derivatives, or mixtures thereof flow rate in (mol/min)]*100. For the purposes of this invention, the term "conversion" means molar conversion, unless otherwise noted.

As used herein, the term "yield" in % is defined as [product flow rate out (mol/min)/hydroxypropionic acid, hydroxypropionic acid derivatives, or mixtures thereof flow rate in (mol/min)]*100. For the purposes of this invention, the term "yield" means molar yield, unless otherwise noted.

As used herein, the term "selectivity" in % is defined as [Yield/Conversion]*100. For the purposes of this invention, the term "selectivity" means molar selectivity, unless otherwise noted.

As used herein, the term "total flow rate out" in mol/min and for hydroxypropionic acid is defined as: (2/3)*[C2 flow rate out (mol/min)]+[C3 flow rate out (mol/min)]+(2/3)*[acetaldehyde flow rate out (mol/min)]+(4/3)*[C4 flow rate out (mol/min)]+[hydroxypropionic acid flow rate out (mol/min)]+[pyruvic acid flow rate out (mol/min)]+(2/3)*[acetic acid flow rate out (mol/min)]+[1,2-propanediol flow rate out (mol/min)]+[propionic acid flow rate out (mol/min)]+[acrylic acid flow rate out (mol/min)]+(5/3)*[2,3-pentanedione flow rate out (mol/min)]+(1/3)*[carbon monoxide flow rate out (mol/min)]+(1/3)*[carbon dioxide flow rate out (mol/min)]. If a hydroxypropionic acid derivative is used instead of hydroxypropionic acid, the above formula needs to be adjusted according to the number of carbon atoms in the hydroxypropionic acid derivative.

As used herein, the term "C2" means ethane and ethylene.

As used herein, the term "C3" means propane and propylene.

As used herein, the term "C4" means butane and butenes.

As used herein, the term "total molar balance" or "TMB" in % is defined as [total flow rate out (mol/min)/hydroxypropionic acid, hydroxypropionic acid derivatives, or mixtures thereof flow rate in (mol/min)]*100.

As used herein, the term "the acrylic acid yield was corrected for TMB" is defined as [acrylic acid yield/total molar balance]*100, to account for slightly higher flows in the reactor.

As used herein, the term "Gas Hourly Space Velocity" or "GHSV" in $h^{-1}$ is defined as [Total gas flow rate (mL/min)/catalyst bed volume (mL)]/60. The total gas flow rate is calculated under Standard Temperature and Pressure conditions (STP; 0° C. and 1 atm).

As used herein, the term "Liquid Hourly Space Velocity" or "LHSV" in $h^{-1}$ is defined as [Total liquid flow rate (mL/min)/catalyst bed volume (mL)]/60.

II Process

The inventors have unexpectedly found that the process of dehydrating hydroxypropionic acid, hydroxypropionic acid derivatives, or mixtures thereof can produce high yield to and selectivity of acrylic acid, acrylic acid derivatives, or mixtures thereof when the solution of hydroxypropionic acid, hydroxypropionic acid derivatives, or mixtures thereof has the hydroxypropionic acid in monomeric form and it is combined with an inert gas, and the process includes an evaporation step and a dehydration step. Furthermore, a cooling step with a short residence time, downstream of the dehydration step, and operating the dehydration step under a pressure of 80 psig or more aid in the achievement of the high yield and selectivity of acrylic acid, acrylic acid derivatives, or mixtures thereof.

A process for converting hydroxypropionic acid, hydroxypropionic acid derivatives, or mixtures thereof to acrylic acid, acrylic acid derivatives, or mixtures thereof of the present invention comprises the following steps: a) providing an aqueous solution comprising hydroxypropionic acid, hydroxypropionic acid derivatives, or mixtures thereof, wherein said hydroxypropionic acid is in monomeric form in the aqueous solution; b) combining the aqueous solution with an inert gas to form an aqueous solution/gas blend; c) evaporating the aqueous solution gas/blend to produce a gaseous mixture; and d) dehydrating the gaseous mixture by contacting the mixture with a dehydration catalyst under a pressure of at least about 80 psig.

Hydroxypropionic acid can be 3-hydroxypropionic acid, 2-hydroxypropionic acid (also called, lactic acid), 2-methyl hydroxypropionic acid, or mixtures thereof. Derivatives of hydroxypropionic acid can be metal or ammonium salts of hydroxypropionic acid, alkyl esters of hydroxypropionic acid, alkyl esters of 2-methyl hydroxypropionic acid, cyclic di-esters of hydroxypropionic acid, hydroxypropionic acid anhydride, or a mixture thereof. Non-limiting examples of metal salts of hydroxypropionic acid are sodium hydroxypropionate, potassium hydroxypropionate, and calcium hydroxypropionate. Non-limiting examples of alkyl esters of hydroxypropionic acid are methyl hydroxypropionate, ethyl hydroxypropionate, butyl hydroxypropionate, 2-ethylhexyl hydroxypropionate, or mixtures thereof. A non-limiting example of cyclic di-esters of hydroxypropionic acid is dilactide.

Hydroxypropionic acid can be in monomeric form or as oligomers in an aqueous solution of hydroxypropionic acid, hydroxypropionic acid derivatives, or mixtures thereof. In one embodiment, the oligomers of the hydroxypropionic acid in an aqueous solution of hydroxypropionic acid, hydroxypropionic acid derivatives, or mixtures thereof are less than about 25 wt % based on the total amount of hydroxypropionic acid, hydroxypropionic acid derivatives, or mixtures thereof. In another embodiment, the oligomers of the hydroxypropionic acid in an aqueous solution of hydroxypropionic acid, hydroxypropionic acid derivatives, or mixtures thereof are less than about 10 wt % based on the total amount of hydroxypropionic acid, hydroxypropionic acid derivatives, or mixtures thereof. In another embodiment, the oligomers of the hydroxypropionic acid in an aqueous solution of hydroxypropionic acid, hydroxypropionic acid derivatives, or mixtures thereof are less than about 5 wt % based on the total amount of hydroxypropionic acid, hydroxypropionic acid derivatives, or mixtures thereof. In yet another embodiment, the hydroxypropionic acid is in monomeric form in an aqueous solution of hydroxypropionic acid, hydroxypropionic acid derivatives, or mixtures thereof. The process steps to remove the oligomers from the aqueous solution can be purification or diluting with water and heating. In one embodiment, the heating step can involve heating the aqueous solution of hydroxypropionic acid, hydroxypropionic acid derivatives, or mixtures thereof at a temperature from about 50° C. to about 100° C. to remove the oligomers of the hydroxypropionic acid. In another embodiment, the heating step can involve heating the lactic acid aqueous solution at a temperature from about 95° C. to about 100° C. to remove the oligomers of the lactic acid and produce a monomeric lactic acid aqueous solution comprising at least 95 wt % of lactic acid in monomeric form based on the total amount of lactic acid. In another embodiment, an about 88 wt % lactic acid aqueous solution (e.g. from Purac Corp., Lincolnshire, Ill.) is diluted with water to form an about 20 wt % lactic acid aqueous solution, to remove the ester impurities that are produced from the intermolecular condensation reaction. These esters can result in loss of product due to their high boiling point and oligomerization in the evaporation stage of the process. Additionally, these esters can cause coking, catalyst deactivation, and reactor plugging. As the water content decreases in the aqueous solution, the loss of feed material to the catalytic reaction, due to losses in the evaporation step, increases.

In one embodiment, the hydroxypropionic acid is lactic acid or 2-methyl lactic acid. In another embodiment, the hydroxypropionic acid is lactic acid. Lactic acid can be L-lactic acid, D-lactic acid, or mixtures thereof. In one embodiment, the hydroxypropionic acid derivative is methyl lactate. Methyl lactate can be neat or in an aqueous solution.

Acrylic acid derivatives can be metal or ammonium salts of acrylic acid, alkyl esters of acrylic acid, acrylic acid oligomers, or a mixture thereof. Non-limiting examples of metal salts of acrylic acid are sodium acrylate, potassium acrylate, and calcium acrylate. Non-limiting examples of alkyl esters of acrylic acid are methyl acrylate, ethyl acrylate, butyl acrylate, 2-ethylhexyl acrylate, or mixtures thereof.

In one embodiment, the concentration of the hydroxypropionic acid, hydroxypropionic acid derivatives, or mixtures thereof in the aqueous solution is between about 5 wt % and about 50 wt %. In another embodiment, the concentration of the hydroxypropionic acid, hydroxypropionic acid derivatives, or mixtures thereof in the aqueous solution is between about 10 wt % and about 25 wt %. In yet another embodiment, the concentration of the hydroxypropionic acid, hydroxypropionic acid derivatives, or mixtures thereof in the aqueous solution is about 20 wt %.

The aqueous solution can be combined with an inert gas to form an aqueous solution/gas blend. Non-limiting examples of the inert gas are air, nitrogen, helium, argon, carbon dioxide, carbon monoxide, steam, and mixtures thereof. The inert gas can be introduced to the evaporating step separately or in combination with the aqueous solution. The aqueous solution can be introduced with a simple tube or through atomization nozzles. Non-limiting examples of atomization nozzles include fan nozzles, pressure swirl atomizers, air blast atomizers, two-fluid atomizers, rotary atomizers, and supercritical carbon dioxide atomizers. In one embodiment, the droplets of the aqueous solution are less than about 500 µm in diameter. In another embodiment, the droplets of the aqueous solution are less than about 200 µm in diameter. In yet another embodiment, the droplets of the aqueous solution are less than about 100 µm in diameter.

In the evaporating step, the aqueous solution/gas blend is heated to give a gaseous mixture. In one embodiment, the temperature during the evaporating step is from about 165° C. to about 450° C. In another embodiment, the temperature during the evaporating step is from about 250° C. to about 375° C. In one embodiment, the gas hourly space velocity (GHSV) in the evaporating step is from about 720 h$^{-1}$ to 3,600 h$^{-1}$. In another embodiment, the gas hourly space velocity (GHSV) in the evaporating step is about 7,200 h$^{-1}$. The evaporating step can be performed at either atmospheric pressure or higher pressure. In one embodiment, the evaporating step is performed under a pressure from about 80 psig to about 550 psig. In another embodiment, the evaporating step is performed under a pressure from about 300 psig to about 400 psig. In yet another embodiment, the evaporating step is performed under a pressure from about 350 psig to about 375 psig. In one embodiment, the gaseous mixture comprises from about 0.5 mol % to about 50 mol % hydroxypropionic acid, hydroxypropionic acid derivatives, or mixtures thereof. In another embodiment, the gaseous mixture comprises from about 1 mol % to about 10 mol % hydroxypropionic acid, hydroxypropionic acid derivatives, or mixtures thereof. In another embodiment, the gaseous mixture comprises from about 1.5 mol % to about 3.5 mol % hydroxypropionic acid, hydroxypropionic acid derivatives, or mixtures thereof. In another embodiment, the gaseous mixture comprises about 2.5 mol % hydroxypropionic acid, hydroxypropionic acid derivatives, or mixtures thereof.

The evaporating step can be performed in various types of equipment, such as, but not limited to, plate heat exchanger, empty flow reactor, and fixed bed flow reactor. Regardless of the type of the reactor, in one embodiment, the reactor has an interior surface comprising material selected from the group consisting of quartz, borosilicate glass, silicon, hastelloy, inconel, manufactured sapphire, stainless steel, and mixtures thereof. In another embodiment, the reactor has an interior surface comprising material selected from the group consisting of quartz, borosilicate glass, and mixtures thereof. The evaporating step can be performed in a reactor with the aqueous solution flowing down, or flowing up, or flowing horizontally. In one embodiment, the evaporating step is performed in a reactor with the aqueous solution flowing down. Also, the evaporating step can be done in a batch form.

The gaseous mixture from the evaporating step is converted to acrylic acid, acrylic acid derivatives, and mixture thereof by contact it with a dehydration catalyst in the dehydrating step. The dehydration catalyst can be selected from the group comprising sulfates, phosphates, metal oxides, aluminates, silicates, aluminosilicates (e.g., zeolites), arsenates, nitrates, vanadates, niobates, tantalates, selenates, arsenatophosphates, phosphoaluminates, phosphoborates, phosphocromates, phosphomolybdates, phosphosilicates, phosphosulfates, phosphotungstates, and mixtures thereof, and others that may be apparent to those having ordinary skill in the art. The catalyst can contain an inert support that is constructed of a material comprising silicates, aluminates, carbons, metal oxides, and mixtures thereof. In one embodiment, the dehydrating step is performed in a reactor, wherein the reactor has an interior surface comprising material selected from the group consisting of quartz, borosilicate glass, silicon, hastelloy, inconel, manufactured sapphire, stainless steel, and mixtures thereof. In another embodiment, the dehydrating step is performed in a reactor, wherein the reactor has an interior surface comprising material selected from the group consisting of quartz, borosilicate glass, and mixtures thereof. In one embodiment, the temperature during the dehydrating step is from about 150° C. to about 500° C. In another embodiment, the temperature during the dehydrating step is from about 300° C. to about 450° C. In one embodiment, the GHSV in the dehydrating step is from about 720 h$^{-1}$ to about 36,000 h$^{-1}$. In another embodiment, the GHSV in the dehydrating step is about 3,600 h$^{-1}$. The dehydrating step can be performed at higher than atmospheric pressure. In one embodiment, the dehydrating step is performed under a pressure of at least about 80 psig. In another embodiment, the dehydrating step is performed under a pressure from about 80 psig to about 550 psig. In another embodiment, the dehydrating step is performed under a pressure from about 150 psig to about 500 psig. In yet another embodiment, the dehydrating step is performed under a pressure from about 300 psig to about 400 psig. The dehydrating step can be performed in a reactor with the gaseous mixture flowing down, flowing up, or flowing horizontally. In one embodiment, the dehydrating step is performed in a reactor with the gaseous mixture flowing down. Also, the dehydrating step can be done in a batch form.

In one embodiment, the evaporating and dehydrating steps are combined in a single step. In another embodiment, the evaporating and dehydrating steps are performed sequentially in a single reactor. In yet another embodiment, the evaporating and dehydrating steps are performed sequentially in a tandem reactor.

In one embodiment, the selectivity of acrylic acid, acrylic acid derivatives, and mixture thereof from hydroxypropionic acid, hydroxypropionic acid derivatives, or mixtures thereof is at least about 50%. In another embodiment, the selectivity of acrylic acid, acrylic acid derivatives, and mixture thereof from hydroxypropionic acid, hydroxypropionic acid derivatives, or mixtures thereof is at least about 80%. In one embodiment, the selectivity of propanoic acid from hydroxypropionic acid, hydroxypropionic acid derivatives, or mixtures thereof is less than about 5%. In another embodiment, the selectivity of propanoic acid from hydroxypropionic acid, hydroxypropionic acid derivatives, or mixtures thereof is less than about 1%. In one embodiment, the conversion of the hydroxypropionic acid, hydroxypropionic acid derivatives, or mixtures thereof is more than about 50%. In another embodiment, the conversion of the hydroxypropionic acid, hydroxypropionic acid derivatives, or mixtures thereof is more than about 80%.

In another embodiment of the present invention, a process for converting hydroxypropionic acid, hydroxypropionic acid derivatives, or mixtures thereof to acrylic acid, acrylic acid derivatives, or mixtures thereof is provided. The process comprises the following steps: a) providing an aqueous solution comprising hydroxypropionic acid, hydroxypropionic acid derivatives, or mixtures thereof, wherein the hydroxypropionic acid comprises oligomers in the aqueous solution; b) heating the aqueous solution at a temperature from about 50° C. to about 100° C. to remove the oligomers of the hydroxypropionic acid and produce an aqueous solution of monomeric hydroxypropionic acid; c) combining the aqueous solution of monomeric hydroxypropionic acid with an inert gas to form an aqueous solution/gas blend; d) evaporating the aqueous solution gas/blend to produce a gaseous mixture; and e) dehydrating the gaseous mixture by contacting the mixture with a dehydration catalyst and producing the acrylic acid, acrylic acid derivatives, or mixtures thereof.

In one embodiment, after the heating step, the concentration of the oligomers of the hydroxypropionic acid in the aqueous solution of monomeric of monomeric hydroxypropionic acid is less than about 20 wt % based on the total amount of hydroxypropionic acid, hydroxypropionic acid derivatives, or mixtures thereof. In another embodiment, after the heating step, the concentration of the oligomers of the hydroxypropionic acid in the aqueous solution of monomeric of monomeric hydroxypropionic acid is less than about 5 wt % based on the total amount of hydroxypropionic acid, hydroxypropionic acid derivatives, or mixtures thereof.

In another embodiment of the present invention, a process for converting hydroxypropionic acid, hydroxypropionic acid derivatives, or mixtures thereof to acrylic acid, acrylic acid derivatives, and mixture thereof is provided. The process comprises the following steps: a) providing an aqueous solution comprising hydroxypropionic acid, hydroxypropionic acid derivatives, or mixtures thereof, wherein the hydroxypropionic acid is in monomeric form in the aqueous solution; b) combining the aqueous solution with an inert gas to form an aqueous solution/gas blend; c) evaporating the aqueous solution/gas blend to produce a gaseous mixture; d) dehydrating the gaseous mixture by contacting the mixture with a dehydration catalyst producing acrylic acid, and/or acrylates; and e) cooling the acrylic acid, acrylic acid derivatives, and mixture thereof at a GHSV of more than about 360 h$^{-1}$.

The stream of acrylic acid, acrylic acid derivatives, and mixture thereof produced in the dehydrating step is cooled to give an aqueous acrylic acid composition as the product stream. The time required to cool stream of the acrylic acid, acrylic acid derivatives, or mixtures thereof must be controlled to reduce the decomposition of acrylic acid to ethylene and polymerization. In one embodiment, the GHSV of the acrylic acid, acrylic acid derivatives, and mixture thereof in the cooling step is more than about 720 h$^{-1}$.

In another embodiment of the present invention, a process for converting lactic acid to acrylic acid is provided. The process comprises the following steps: a) diluting an about 88 wt % lactic acid aqueous solution with water to form an about 20 wt % lactic acid aqueous solution; b) heating the about 20 wt % lactic acid aqueous solution at a temperature of about 95° C. to about 100° C. to remove oligomers of the lactic acid, producing a monomeric lactic acid solution comprising at least about 95 wt % of the lactic acid in monomeric form based on the total amount of lactic acid; c) combining the monomeric lactic acid solution with nitrogen to form an aqueous solution/gas blend; d) evaporating the aqueous solution/gas blend in a reactor with inside surface of borosilicate glass at a GHSV of about 7,200 h$^{-1}$ at a temperature from about 300° C. to about 350° C. to produce a gaseous mixture comprising about 2.5 mol % lactic acid and about 50 mol % water; e) dehydrating the gaseous mixture in a reactor with inside surface of borosilicate glass at a GHSV of about 3,600 h$^{-1}$ at a temperature of 350° C. to about 425° C. by contacting the mixture with a dehydration catalyst under a pressure of about 360 psig, producing the acrylic acid; and f) cooling the acrylic acid at a GHSV from about 360 h$^{-1}$ to about 36,000 h$^{-1}$.

In another embodiment of the present invention, a process for converting hydroxypropionic acid, derivatives of hydroxypropionic acid, and mixtures thereof to acrylic acid, acrylic acid derivatives, or mixtures thereof is provided. The process comprises the following steps: a) providing an aqueous solution comprising hydroxypropionic acid, hydroxypropionic acid derivatives, or mixtures thereof, wherein the hydroxypropionic acid is in monomeric form in the aqueous solution, and wherein the hydroxypropionic acid, hydroxypropionic acid derivatives, or mixtures thereof comprise from about 10 wt % to about 25 wt % of the aqueous solution; b) combining the aqueous solution with an inert gas to form an aqueous solution/gas blend; c) evaporating the aqueous solution/gas blend to produce a gaseous mixture; and d) dehydrating the gaseous mixture by contacting the mixture with a dehydration catalyst producing acrylic acid, acrylic acid derivatives, or mixtures thereof.

In another embodiment of the present invention, a process for converting alkyl lactates to acrylic acid, acrylic acid derivatives, or mixtures thereof is provided. The process comprises the following steps: a) providing alkyl lactates or a solution comprising alkyl lactates and a solvent; b) combining said alkyl lactates or said solution comprising said alkyl lactates and said solvent with an inert gas to form a liquid/gas blend; c) evaporating said liquid/gas blend to produce a gaseous mixture; and d) dehydrating said gaseous mixture by contacting said gaseous mixture with a dehydration catalyst under a pressure of at least about 80 psig, producing acrylic acid, acrylic acid derivatives, or mixtures thereof.

In one embodiment, alkyl lactates are selected from the group consisting of methyl lactate, ethyl lactate, butyl lactate, 2-ethylhexyl lactate, and mixtures thereof. In another embodiment, the solvent is selected from the group consisting of water, methanol, ethanol, butanol, 2-ethylhexanol, isobutanol, isooctyl alcohol, and mixtures thereof.

III Catalysts for the Conversion of Hydroxypropionic Acid or its Derivatives to Acrylic Acid or its Derivatives In one embodiment, the catalyst comprises: (a) at least one condensed phosphate anion selected from the group consisting of formulae (I), (II), and (III), $$[P_nO_{3n+1}]^{(n+2)-} \quad (I)$$

$$[P_nO_{3n}]^{n-} \quad (II)$$

$$[P_{(2m+n)}O_{(5m+3n)}]^{n-} \quad (III)$$

wherein n is at least 2 and m is at least 1, and (b) at least two different cations, wherein the catalyst is essentially neutrally charged, and further, wherein the molar ratio of phosphorus to the at least two different cations is between about 0.7 and about 1.7.

The anions defined by formulae (I), (II), and (III) are also referred to as polyphosphates (or oligophosphates), cyclophosphates, and ultraphosphates, respectively.

In another embodiment, the catalyst comprises: (a) at least one condensed phosphate anion selected from the group consisting of formulae (I) and (II), $$[P_nO_{3n+1}]^{(n+2)-} \quad (I)$$

$$[P_nO_{3n}]^{n-} \quad (II)$$

wherein n is at least 2, and (b) at least two different cations, wherein the catalyst is essentially neutrally charged, and further, wherein the molar ratio of phosphorus to the at least two different cations is between about 0.7 and about 1.7.

The cations can be monovalent or polyvalent. In one embodiment, one cation is monovalent and the other cation is polyvalent. In another embodiment, the polyvalent cation is selected from the group consisting of divalent cations, trivalent cations, tetravalent cations, pentavalent cations, and mixtures thereof. Non-limiting examples of monovalent cations are $H^+$, $Li^+$, $Na^+$, $K^+$, $Rb^+$, $Cs^+$, $Ag^+$, $Rb^+$, $Tl^+$, and mixtures thereof. In one embodiment, the monovalent cation is selected from the group consisting of $Li^+$, $Na^+$, $K^+$, $Rb^+$, $Cs^+$, and mixtures thereof; in another embodiment, the monovalent cation is $Na^+$ or $K^+$; and in yet another embodiment, the monovalent cation is $K^+$. Non-limiting examples of polyvalent cations are cations of the alkaline earth metals (i.e., Be, Mg, Ca, Sr, Ba, and Ra), transition metals (e.g. Y, Ti, Zr, V, Nb, Cr, Mo, Mn, Re, Fe, Ru, Co, Rh, Ni, Pd, Pt, Cu, Ag, and Au), poor metals (e.g. Zn, Ga, Si, Ge, B, Al, In, Sb, Sn, Bi, and Pb), lanthanides (e.g. La and Ce), and actinides (e.g. Ac and Th). In one embodiment, the polyvalent cation is selected from the group consisting of $Be^{2+}$, $Mg^{2+}$, $Ca^{2+}$, $Sr^{2+}$, $Ba^{2+}$, $Mn^{2+}$, $Fe^{2+}$, $Co^{2+}$, $Ni^{2+}$, $Cu^{2+}$, $Zn^{2+}$, $Cd^{2+}$, $Sn^{2+}$, $Pb^{2+}$, $Ti^{3+}$, $Cr^{3+}$, $Mn^{3+}$, $Fe^{3+}$, $Al^{3+}$, $Ga^{3+}$, $Y^{3+}$, $In^{3+}$, $Sb^{3+}$, $Bi^{3+}$, $Si^{4+}$, $Ti^{4+}$, $V^{4+}$, $Ge^{4+}$, $Mo^{4+}$, $Pt^{4+}$, $V^{5+}$, $Nb^{5+}$, $Sb^{5+}$, and mixtures thereof. In one embodiment, the polyvalent cation is selected from the group consisting of $Ca^{2+}$, $Ba^{2+}$, $Cu^{2+}$, $Mn^{2+}$, $Mn^{3+}$, and mixtures thereof; in another embodiment, the polyvalent cation is selected from the group consisting of $Ca^{2+}$, $Ba^{2+}$, $Mn^{3+}$, and mixtures thereof; and in yet another embodiment, the polyvalent cation is $Ba^{2+}$.

The catalyst can include cations: (a) $H^+$, $Li^+$, $Na^+$, $K^+$, $Rb^+$, $Cs^+$, or mixtures thereof; and (b) $Be^{2+}$, $Mg^{2+}$, $Ca^{2+}$, $Sr^{2+}$, $Ba^{2+}$, $Mn^{2+}$, $Fe^{2+}$, $Co^{2+}$, $Ni^{2+}$, $Cu^{2+}$, $Zn^{2+}$, $Cd^{2+}$, $Sn^{2+}$, $Pb^{2+}$, $Ti^{3+}$, $Cr^{3+}$, $Mn^{3+}$, $Fe^{3+}$, $Al^{3+}$, $Ga^{3+}$, $Y^{3+}$, $In^{3+}$, $Sb^{3+}$, $Bi^{3+}$, $Si^{4+}$, $Ti^{4+}$, $V^{4+}$, $Ge^{4+}$, $Mo^{4+}$, $Pt^{4+}$, $V^{5+}$, $Nb^{5+}$, $Sb^{5+}$, or mixtures thereof. In one embodiment the catalyst comprises $Li^+$, $Na^+$, or $K^+$ as monovalent cation, and $Ca^{2+}$, $Ba^{2+}$, or $Mn^{3+}$ as polyvalent cation; in another embodiment, the catalyst comprises $Na^+$ or $K^+$ as monovalent cation, and $Ca^{2+}$ or $Ba^{2+}$ as polyvalent cation; and in yet another embodiment, the catalyst comprises $K^+$ as the monovalent cation and $Ba^{2+}$ as the polyvalent cation.

In one embodiment, the catalyst comprises $Ba_{2-x-s}K_{2x}H_{2s}P_2O_7$ and $(KPO_3)_n$, wherein x and s are greater or equal to 0 and less than about 0.5 and n is a positive integer. In another embodiment, the catalyst comprises $Ca_{2-x-s}K_{2x}H_{2s}P_2O_7$ and $(KPO_3)_n$, wherein x and s are greater or equal to 0 and less than about 0.5 and n is a positive integer. In yet another embodiment, the catalyst comprises $Mn_{1-x-s}K_{1+3x}H_{3s}P_2O_7$ or $Mn_{1-x-s}K_{2+2x}H_{2s}P_2O_7$ and $(KPO_3)$ wherein x and s are greater or equal to 0 and less than about 0.5 and n is a positive integer. In another embodiment, the catalyst comprises any blend of $Ba_{2-x-s}K_{2x}H_{2s}P_2O_7$, $Ca_{2-x-s}K_{2x}H_{2s}P_2O_7$, $Mn_{1-x-s}K_{1+3x}H_{3s}P_2O_7$ or $Mn_{1-x-s}K_{2+2x}H_{2s}P_2O_7$; and $(KPO_3)_n$, wherein x and s are greater or equal to 0 and less than about 0.5 and n is a positive integer.

In one embodiment, the molar ratio of phosphorus to the cations in the catalyst is between about 0.7 and about 1.7; in another embodiment, the molar ratio of phosphorus to the cations in the catalyst is between about 0.8 and about 1.3; and in yet another embodiment, the molar ratio of phosphorus to the cations in the catalyst is about 1.

In one embodiment, the catalyst comprises: (a) at least two different condensed phosphate anions selected from the group consisting of formulae (I), (II), and (III), $$[P_nO_{3n+1}]^{(n+2)-} \quad (I)$$

$$[P_nO_{3n}]^{n-} \quad (II)$$

$$[P_{(2m+n)}O_{(5m+3n)}]^{n-} \quad (III)$$

wherein n is at least 2 and m is at least 1, and (b) one cation, wherein the catalyst is essentially neutrally charged, and further, wherein the molar ratio of phosphorus to the cation is between about 0.5 and about 4.0. In another embodiment, the molar ratio of phosphorus to the cation is between about t/2 and about t, wherein t is the charge of the cation.

The catalyst can include an inert support that is constructed of a material comprising silicates, aluminates, carbons, metal oxides, and mixtures thereof. Alternatively, the carrier is inert relative to the reaction mixture expected to contact the catalyst. In the context of the reactions expressly described herein, in one embodiment the carrier is a low surface area silica or zirconia. When present, the carrier represents an amount of about 5 wt % to about 98 wt %, based on the total weight of the catalyst. Generally, a catalyst that includes an inert support can be made by one of two exemplary methods: impregnation or co-precipitation. In the impregnation method, a suspension of the solid inert support is treated with a solution of a pre-catalyst, and the resulting material is then activated under conditions that will convert the pre-catalyst to a more active state. In the co-precipitation method, a homogenous solution of the catalyst ingredients is precipitated by the addition of additional ingredients.

In another embodiment, the catalyst can be sulfate salts; phosphate salts; mixtures of sulfate and phosphate salts; bases; zeolites or modified zeolites; metal oxides or modified metal oxides; supercritical water, or mixtures thereof.

IV Catalyst Preparation Methods

In one embodiment, the method of preparing the catalyst includes mixing and heating at least two different phosphorus containing compounds, wherein each said compound is described by one of the formulae (IV) to (XXV), or any of the hydrated forms of said formulae:

$$M^I_y(H_{3-y}PO_4) \quad (IV)$$

$$M^{II}_y(H_{3-y}PO_4)_2 \quad (V)$$

$$M^{III}_y(H_{3-y}PO_4)_3 \quad (VI)$$

$$M^{IV}_y(H_{3-y}PO_4)_4 \quad (VII)$$

$$(NH_4)_y(H_{3-y}PO_4) \quad (VIII)$$

$$M^{II}_a(OH)_b(PO_4)_c \quad (IX)$$

$$M^{III}_d(OH)_e(PO_4)_f \quad (X)$$

$$M^{II}M^IPO_4 \quad (XI)$$

$$M^{III}M^I_3(PO_4)_2 \quad (XII)$$

$$M^{IV}_2M^I(PO_4)_3 \quad (XIII)$$

$$M^I_zH_{4-z}P_2O_7 \quad (XIV)$$

$$M^{II}_vH_{(4-2v)}P_2O_7 \quad (XV)$$

$$M^{IV}P_2O_7 \quad (XVI)$$

$$(NH_4)_zH_{4-z}P_2O_7 \quad (XVII)$$

$$M^{III}M^IP_2O_7 \quad (XVIII)$$

$$M^IH_w(PO_3)_{(1+w)} \quad (XIX)$$

$$M^{II}H_w(PO_3)_{(2+w)} \quad (XX)$$

$$M^{III}H_w(PO_3)_{(3+w)} \quad (XXI)$$

$$M^{IV}H_w(PO_3)_{(4+w)} \quad (XXII)$$

$$M^{II}_gM^I_h(PO_3)_i \quad (XXIII)$$

$$M^{III}_jM^I_k(PO_3)_l \quad (XXIV)$$

$$P_2O_5 \quad (XXV)$$

wherein $M^I$ is a monovalent cation; wherein $M^{II}$ is a divalent cation; wherein $M^{III}$ is a trivalent cation; wherein $M^{IV}$ is a tetravalent cation; wherein y is 0, 1, 2, or 3; wherein z is 0, 1, 2, 3, or 4; wherein v is 0, 1, or 2; wherein w is 0 or any positive integer; and wherein a, b, c, d, e, f, g, h, i, j, k, and l are any positive integers, such that the equations: $2a=b+3c$, $3d=e+3f$, $i=2g+h$, and $l=3j+k$ are satisfied.

In one embodiment, the catalyst is prepared by mixing and heating one or more phosphorus containing compounds of formula (IV), wherein y is equal to 1, and one or more phosphorus containing compounds of formula (V), wherein y is equal to 2. In another embodiment, the catalyst is prepared by mixing and heating $M^I H_2 PO_4$ and $M^{II} HPO_4$. In one embodiment, $M^I$ is $K^+$ and $M^{II}$ is $Ca^{2+}$, i.e., the catalyst is prepared by mixing and heating $KH_2PO_4$ and $CaHPO_4$; or $M^I$ is K and $M^{II}$ is $Ba^{2+}$, i.e., the catalyst is prepared by mixing and heating $KH_2PO_4$ and $BaHPO_4$.

In one embodiment, the catalyst is prepared by mixing and heating one or more phosphorus containing compound of formula (IV), wherein y is equal to 1, one or more phosphorus containing compounds of formula (XV), wherein v is equal to 2. In another embodiment, the catalyst is prepared by mixing and heating $M^I H_2 PO_4$ and $M^{II}_2 P_2 O_7$. In one embodiment, $M^I$ is $K^+$ and $M^{II}$ is $Ca^{2+}$, i.e., the catalyst is prepared by mixing and heating $KH_2PO_4$ and $Ca_2P_2O_7$; or $M^I$ is $K^+$ and $M^{II}$ is $Ba^{2+}$, i.e., the catalyst is prepared by mixing and heating $KH_2PO_4$ and $Ba_2P_2O_7$.

In another embodiment, the molar ratio of phosphorus to the cations in the catalyst is between about 0.7 and about 1.7; in yet another embodiment, the molar ratio of phosphorus to the cations in the catalyst is between about 0.8 and about 1.3; and in another embodiment, the molar ratio of phosphorus to the cations in the catalyst is about 1.

In another embodiment, the method of preparing the catalyst includes mixing and heating (a) at least one phosphorus containing compound, wherein each said compound is described by one of the formulae (IV) to (XXV), or any of the hydrated forms of said formulae:

$$M^I_y(H_{3-y}PO_4) \quad (IV)$$

$$M^{II}_y(H_{3-y}PO_4)_2 \quad (V)$$

$$M^{III}_y(H_{3-y}PO_4)_3 \quad (VI)$$

$$M^{IV}_y(H_{3-y}PO_4)_4 \quad (VII)$$

$$(NH_4)_y(H_{3-y}PO_4) \quad (VIII)$$

$$M^{II}_a(OH)_b(PO_4)_c \quad (IX)$$

$$M^{III}_d(OH)_e(PO_4)_f \quad (X)$$

$$M^{II}M^I PO_4 \quad (XI)$$

$$M^{III}M^I_3(PO_4)_2 \quad (XII)$$

$$M^{IV}_2 M^I(PO_4)_3 \quad (XIII)$$

$$M^I_z H_{4-z} P_2 O_7 \quad (XIV)$$

$$M^{II}_v H_{(4-2v)} P_2 O_7 \quad (XV)$$

$$M^{IV} P_2 O_7 \quad (XVI)$$

$$(NH_4)_z H_{4-z} P_2 O_7 \quad (XVII)$$

$$M^{III} M^I P^2 O_7 \quad (XVIII)$$

$$M^I H_w(PO_3)_{(1+w)} \quad (XIX)$$

$$M^I H_w(PO_3)_{(2+w)} \quad (XX)$$

$$M^{III} H_w(PO_3)_{(3+w)} \quad (XXI)$$

$$M^{IV} H_w(PO_3)_{(4+w)} \quad (XXII)$$

$$M^{II}_g M^I_h (PO_3)_i \quad (XXIII)$$

$$M^{III}_j M^I_k (PO_3)_l \quad (XXIV)$$

$$P_2 O_5 \quad (XXV)$$

wherein y is 0, 1, 2, or 3; wherein z is 0, 1, 2, 3, or 4; wherein v is 0, 1, or 2; wherein w is 0 or any positive integer; and wherein a, b, c, d, e, f, g, h, i, j, k, and l are any positive integers, such that the equations: $2a=b+3c$, $3d=e+3f$, $i=2g+h$, and $l=3j+k$ are satisfied, and (b) at least one non-phosphorus containing compound selected from the group consisting of nitrate salts, carbonate salts, acetate salts, metal oxides, chloride salts, sulfate salts, and metal hydroxides, wherein each said compound is described by one of the formulae (XXVI) to (XL), or any of the hydrated forms of said formulae:

$$M^I NO_3 \quad (XXVI)$$

$$M^{II}(NO_3)_2 \quad (XXVII)$$

$$M^{III}(NO_3)_3 \quad (XXVIII)$$

$$M^I_2 CO_3 \quad (XXIX)$$

$$M^{II} CO_3 \quad (XXX)$$

$$M^{III}_2 (CO_3)_3 \quad (XXXI)$$

$$(CH_3COO)M^I \quad (XXXII)$$

$$(CH_3COO)_2 M^{II} \quad (XXXIII)$$

$$(CH_3COO)_3 M^{III} \quad (XXXIV)$$

$$(CH_3COO)_4 M^{IV} \quad (XXXV)$$

$$M^I_2 O \quad (XXXVI)$$

$$M^{II} O \quad (XXXVII)$$

$$M^{III}_2 O_3 \quad (XXXVIII)$$

$$M^{IV} O_2 \quad (XXXIX)$$

$$M^I Cl \quad (XXXX)$$

$$M^{II} Cl_2 \quad (XXXXI)$$

$$M^{III} Cl_3 \quad (XXXXII)$$

$$M^{IV} Cl_4 \quad (XXXXIII)$$

$$M^I_2 SO_4 \quad (XXXXIV)$$

$$M^{II} SO_4 \quad (XXXXV)$$

$$M^{III}_2 (SO_4)_3 \quad (XXXXVI)$$

$$M^{IV}(SO_4)_2 \quad (XXXXVII)$$

$$M^I OH \quad (XXXVIII)$$

$$M^{II}(OH)_2 \quad (XXXIX)$$

$$M^{III}(OH)_3 \quad (XL).$$

In another embodiment, the non-phosphorus containing compounds can be selected from the group consisting of carboxylic acid-derived salts, halide salts, metal acetylacetonates, and metal alkoxides.

In one embodiment of the present invention, the molar ratio of phosphorus to the cations in the catalyst is between about 0.7 and about 1.7; in another embodiment, the molar ratio of phosphorus to the cations in the catalyst is between about 0.8 and about 1.3; and in yet another embodiment, the molar ratio of phosphorus to the cations in the catalyst is about 1.

In another embodiment of the present invention, the catalyst is prepared by mixing and heating one or more phosphorus containing compounds of formulae (IV) to (XXV) or their hydrated forms, and one or more nitrate salts of formulae (XXVI) to (XXVIII) or their hydrated forms. In another embodiment of the present invention, the catalyst is prepared by mixing and heating one or more phosphorus containing compounds of formula (IV) and one or more nitrate salts of formula (XXVII). In a further embodiment of the present invention, the catalyst is prepared by mixing and heating a phosphorus containing compound of formula (IV) wherein y is equal to 2, a phosphorus containing compound of formula (IV) wherein y is equal to 0 (i.e., phosphoric acid), and a nitrate salt of formula (XXVII). In yet another embodiment of the present invention, the catalyst is prepared by mixing and heating $K_2HPO_4$, $H_3PO_4$, and $Ba(NO_3)_2$. In yet another embodiment, the catalyst is prepared by mixing and heating $K_2HPO_4$, $H_3PO_4$, and $Ca(NO_3)_2$.

In one embodiment of the present invention, the catalyst is prepared by mixing and heating one or more phosphorus containing compounds of formula (IV) and one or more nitrate salts of formula (XXVIII). In a further embodiment of the present invention, the catalyst is prepared by mixing and heating a phosphorus containing compound of formula (IV) wherein y is equal to 2, a phosphorus containing compound of formula (IV) wherein y is equal to 0 (i.e., phosphoric acid), and a nitrate salt of formula (XXVIII). In yet another embodiment of the present invention, the catalyst is prepared by mixing and heating $K_2HPO_4$, $H_3PO_4$, and $Mn(NO_3)_2 \cdot 4H_2O$.

In one embodiment of the present invention, the catalyst is prepared by mixing and heating one or more phosphorus containing compounds of formula (V) and one or more nitrate salts of formula (XXVI). In another embodiment of the present invention, the catalyst is prepared by mixing and heating a phosphorus containing compound of formula (V) wherein y is equal to 2, a phosphorus containing compound of formula (V) wherein y is equal to 0 (i.e., phosphoric acid), and a nitrate salt of formula (XXVI). In yet another embodiment of the present invention, the catalyst is prepared by mixing and heating $BaHPO_4$, $H_3PO_4$, and $KNO_3$. In another embodiment, the catalyst is prepared by mixing and heating $CaHPO_4$, $H_3PO_4$, and $KNO_3$.

In one embodiment of this invention, the catalyst is prepared by mixing and heating one or more phosphorus containing compounds of formula (V), one or more phosphorus containing compounds of formula (XV), and one or more nitrate salts of formula (XXVI). In a further embodiment of this invention, the catalyst is prepared by mixing and heating a phosphorus containing compound of formula (V), wherein y is equal to 0 (i.e., phosphoric acid); a phosphorus containing compound of formula (XV), wherein v is equal to 2; and a nitrate salt of formula (XXVI). In another embodiment of the present invention, the catalyst is prepared by mixing and heating $H_3PO_4$, $Ca_2P_2O_7$, and $KNO_3$. In yet another embodiment, the catalyst is prepared by mixing and heating $H_3PO_4$, $Ba_2P_2O_7$, and $KNO_3$.

In another embodiment of this invention, the catalyst is prepared by mixing and heating one or more phosphorus containing compounds of formula (VI) and one or more nitrate salts of formula (XXVI). In another embodiment of this invention, the catalyst is prepared by mixing and heating a phosphorus containing compound of formula (VI), wherein y is equal to 3; a phosphorus containing compound of formula (VI), wherein y is equal to 0 (i.e., phosphoric acid); and a nitrate salt of formula (XXVI). In yet another embodiment of this invention, the catalyst is prepared by mixing and heating $MnPO_4 \cdot qH_2O$, $H_3PO_4$, and $KNO_3$.

In one embodiment of this invention, the catalyst is prepared by mixing and heating one or more phosphorus containing compounds of formula (IV), one or more phosphorus containing compounds of formula (IX), and one or more nitrate salts of formula (XXVII). In another embodiment of this invention, the catalyst is prepared by mixing and heating a phosphorus containing compound of formula (IV), wherein y is equal to 2; a phosphorus containing compound of formula (IV), wherein y is equal to 0 (i.e., phosphoric acid); a phosphorus containing compound of formula (IX), wherein a is equal to 2, b is equal to 1, and c is equal to 1; and a nitrate salt of formula (XXVII). In yet another embodiment of this invention, the catalyst is prepared by mixing and heating $K_2HPO_4$, $H_3PO_4$, $Cu_2(OH)PO_4$, and $Ba(NO_3)_2$.

In one embodiment of this invention, the catalyst is prepared by mixing and heating one or more phosphorus containing compounds of formula (V), one or more phosphorus containing compounds of formula (IX), and one or more nitrate salts of formula (XXVI). In another embodiment of this invention, the catalyst is prepared by mixing and heating a phosphorus containing compound of formula (V), wherein y is equal to 3; a phosphorus containing compound of formula (V), wherein y is equal to 0 (i.e., phosphoric acid); a phosphorus containing compound of formula (IX), wherein a is equal to 2, b is equal to 1, and c is equal to 1; and a nitrate salt of formula (XXVI). In yet another embodiment, the catalyst is prepared by mixing and heating $Ba_3(PO_4)_2$, $H_3PO_4$, $Cu_2(OH)PO_4$, and $KNO_3$.

In one embodiment of the present invention, the catalyst is prepared by mixing and heating one or more phosphorus containing compounds described by one of the formulae (IV) to (XXV) or any of the hydrated forms, and one or more carbonate salts described by one of the formulae (XXIX) to (XXXI) or any of the hydrated forms.

In one embodiment of the present invention, the catalyst is prepared by mixing and heating one or more phosphorus containing compounds described by one of the formulae (IV) to (XXV) or any of the hydrated forms, and one or more acetate salts described by one of the formulae (XXXII) to (XXXV), any other organic acid-derived salts, or any of the hydrated forms.

In one embodiment of the present invention, the catalyst is prepared by mixing and heating one or more phosphorus containing compounds described by one of the formulae (IV) to (XXV) or any of the hydrated forms, and one or more metal oxides described by one of the formulae (XXXVI) to (XXXIX) or any of the hydrated forms.

In one embodiment of the present invention, the catalyst is prepared by mixing and heating one or more phosphorus containing compounds described by one of the formulae (IV) to (XXV) or any of the hydrated forms, and one or more chloride salts described by one of the formulae (XXXX) to (XXXXIII), any other halide salts, or any of the hydrated forms.

In one embodiment of the present invention, the catalyst is prepared by mixing and heating one or more phosphorus containing compounds described by one of the formulae (IV) to (XXV) or any of the hydrated forms, and one or more sulfate salts described by one of the formulae (XXXXIV) to (XXXXVII) or any of the hydrated forms.

In one embodiment of the present invention, the catalyst is prepared by mixing and heating one or more phosphorus containing compounds described by one of the formulae (IV) to (XXV) or any of the hydrated forms, and one or more hydroxides described by one of the formulae (XXXXVIII) to (XL) or any of the hydrated forms.

In one embodiment of the present invention, the catalyst is prepared by mixing and heating one or more phosphorus containing compounds of formulae (IV) to (XXV), and two or more non-phosphorus containing compounds of formulae (XXVI) to (XL) or their hydrated forms.

In one embodiment, the molar ratio of phosphorus to the cations (i.e., $M^I + M^{II} + M^{III} + \ldots$) is between about 0.7 and about 1.7; in another embodiment, the molar ratio of phosphorus to the cations (i.e., $M^I + M^{II} + M^{III} + \ldots$) is between about 0.8 and about 1.3, and in yet another embodiment, the molar ratio of phosphorus to the cations (i.e., $M^I + M^{II} + M^{III} + \ldots$) is about 1. For example, in an embodiment when the catalyst includes potassium ($K^+$) and barium ($Ba^{2+}$), the molar ratio between phosphorus and the metals (K+Ba) is between about 0.7 and about 1.7; and in another embodiment, the molar ratio between phosphorus and the metals (K+Ba) is about 1.

When the catalyst includes only two different cations, the molar ratio between cations is, in one embodiment, between about 1:50 and about 50:1; and in another embodiment, the molar ratio between cations is between about 1:4 and about 4:1. For example, when the catalyst includes potassium ($K^+$) and barium ($Ba^{2+}$), the molar ratio between them (K:Ba), in one embodiment, is between about 1:4 and about 4:1. Also, when the catalyst is prepared by mixing and heating $K_2HPO_4$, $Ba(NO_3)_2$, and $H_3PO_4$, the potassium and barium are present, in another embodiment, in a molar ratio, K:Ba, between about 2:3 to about 1:1.

In one embodiment, the catalyst can include an inert support that is constructed of a material comprising silicates, aluminates, carbons, metal oxides, and mixtures thereof. Alternatively, the carrier is inert relative to the reaction mixture expected to contact the catalyst. In another embodiment, the method of preparing the catalyst can further include mixing an inert support with the catalyst before, during, or after the mixing and heating of the phosphorus containing compounds, wherein the inert support includes silicates, aluminates, carbons, metal oxides, and mixtures thereof. In yet another embodiment, the method of preparing the catalyst can further include mixing an inert support with the catalyst before, during, or after the mixing and heating of the phosphorus containing compounds and the non-phosphorus containing compounds, wherein the inert support includes silicates, aluminates, carbons, metal oxides, and mixtures thereof.

Mixing of the phosphorus containing compounds or the phosphorus containing and non-phosphorus containing compounds of the catalyst can be performed by any method known to those skilled in the art, such as, by way of example and not limitation: solid mixing and co-precipitation. In the solid mixing method, the various components are physically mixed together with optional grinding using any method known to those skilled in the art, such as, by way of example and not limitation, shear, extensional, kneading, extrusion, and others. In the co-precipitation method, an aqueous solution or suspension of the various components, including one or more of the phosphate compounds, is prepared, followed by optional filtration and heating to remove solvents and volatile materials (e.g., water, nitric acid, carbon dioxide, ammonia, or acetic acid). The heating is typically done using any method known to those skilled in the art, such as, by way of example and not limitation, convection, conduction, radiation, microwave heating, and others.

In one embodiment of the invention, the catalyst is calcined. Calcination is a process that allows chemical reaction and/or thermal decomposition and/or phase transition and/or removal of volatile materials. The calcination process is carried out with any equipment known to those skilled in the art, such as, by way of example and not limitation, furnaces or reactors of various designs, including shaft furnaces, rotary kilns, hearth furnaces, and fluidized bed reactors. The calcination temperature is, in one embodiment, about 200° C. to about 1200° C.; in another embodiment, the calcination temperature is about 250° C. to about 900° C.; and in yet another embodiment, the calcination temperature is about 300° C. to 600° C. The calcination time is, in one embodiment, about one hour to about seventy-two hours.

While many methods and machines are known to those skilled in the art for fractionating particles into discreet sizes and determining particle size distribution, sieving is one of the easiest, least expensive, and common ways. An alternative way to determine the size distribution of particles is with light scattering. Following calcination, the catalyst is, in one embodiment, ground and sieved to provide a more uniform product. The particle size distribution of the catalyst particles includes a particle span that, in one embodiment, is less than about 3; in another embodiment, the particle size distribution of the catalyst particles includes a particle span that is less than about 2; and in yet another embodiment, the particle size distribution of the catalyst particles includes a particle span that is less than about 1.5. In another embodiment of the invention, the catalyst is sieved to a median particle size of about 50 μm to about 500 μm. In another embodiment of the invention, the catalyst is sieved to a median particle size of about 100 μm to about 200 μm.

In another embodiment, the catalyst is prepared by the following steps, which comprise: (a) combining a phosphorus containing compound, a nitrate salt, phosphoric acid, and water to form a wet mixture, wherein the molar ratio between phosphorus and the cations in both said phosphorus containing compound and said nitrate salt is about 1, (b) calcining said wet mixture stepwise at about 50° C., about 80° C., about 120° C., and about 450° C. to about 550° C. to produce a dried solid, and (c) grinding and sieving said dried solid to about 100 μm to about 200 μm, to produce said catalyst.

In another embodiment, the catalyst is prepared by the following steps, which comprise: (a) combining $MnPO_4qH_2O$, $KNO_3$, and $H_3PO_4$, in a molar ratio of about 0.3:1:1, on an anhydrous basis, and water to give a wet mixture, (b) calcining said wet mixture stepwise at about 50° C., about 80° C., about 120° C., and about 450° C. to about 550° C. to give a dried solid, and (c) grinding and sieving said dried solid to about 100 μm to about 200 μm, to produce said catalyst.

In another embodiment, the catalyst is prepared by the following steps, which comprise: (a) combining $Ca_2P_2O_7$, $KNO_3$, and $H_3PO_4$, in a molar ratio of about 1.6:1:1, and water to give a wet mixture, (b) calcining said wet mixture stepwise at about 50° C., about 80° C., about 120° C., and about 450° C. to about 550° C. to give a dried solid, and (c) grinding and sieving said dried solid to about 100 μm to about 200 μm, to produce said catalyst.

In another embodiment, the catalyst is prepared by the following steps, which comprise: (a) combining a phosphorus containing compound, a nitrate salt, phosphoric acid, and water to give a wet mixture, wherein the molar ratio between phosphorus and the cations in both the phosphorus containing compound and nitrate salt is about 1, (b) heating said wet mixture to about 80° C. with stirring until near dryness to form a wet solid, (c) calcining said wet solid stepwise at about 50° C., about 80° C., about 120° C., and about 450° C. to about 550° C. to give a dried solid, and (d) grinding and sieving said dried solid to about 100 μm to about 200 μm, to produce said catalyst.

In another embodiment, the catalyst is prepared by the following steps, which comprise: (a) combining $B_a(NO_3)_2$, $K_2HPO_4$, and $H_3PO_4$, in a molar ratio of about 3:1:4, and water to give a wet mixture, (b) heating said wet mixture to about 80° C. with stirring until near dryness to form a wet solid, (c) calcining said wet solid stepwise at about 50° C., about 80° C., about 120° C., and about 450° C. to about 550° C. to give a dried solid, and (d) grinding and sieving said dried solid to about 100 μm to about 200 μm, to produce said catalyst.

In another embodiment, the catalyst is prepared by the following steps, which comprise: (a) combining $Mn(NO_3)_2 \cdot 4H_2O$, $K_2HPO_4$, and $H_3PO_4$, in a molar ratio of about 1:1.5:2, and water to give a wet mixture, (b) heating said wet mixture to about 80° C. with stirring until near dryness to form a wet solid, (c) calcining said wet solid stepwise at about 50° C., about 80° C., about 120° C., and about 450° C. to about 550° C. to give a dried solid, and (d) grinding and sieving said dried solid to about 100 μm to about 200 μm, to produce said catalyst.

In another embodiment, the catalyst is prepared by the following steps, which comprise: (a) combining $Ca_2P_2O_7$ and $KH_2PO_4$ in a molar ratio of about 3:1 to give a solid mixture, and (b) calcining said solid mixture stepwise at about 50° C., about 80° C., about 120° C., and about 450° C. to about 550° C., to produce said catalyst.

Following calcination and optional grinding and sieving, the catalyst can be utilized to catalyze several chemical reactions. Non-limiting examples of reactions are: dehydration of hydroxypropionic acid to acrylic acid (as described in further detail below), dehydration of glycerin to acrolein, dehydration of aliphatic alcohols to alkenes or olefins, dehydrogenation of aliphatic alcohols to ethers, other dehydrogenations, hydrolyses, alkylations, dealkylations, oxidations, disproportionations, esterifications, cyclizations, isomerizations, condensations, aromatizations, polymerizations, and other reactions that may be apparent to those having ordinary skill in the art.

V EXAMPLES

The following examples are provided to illustrate the invention, but are not intended to limit the scope thereof.

Example 1

Solid dibasic potassium phosphate, $K_2HPO_4$ (36.40 g, 209 mmol, ≥98%; Sigma Aldrich Co., St. Louis, Mo.; catalog # P3786) was mixed quickly with an aqueous solution of barium nitrate, $Ba(NO_3)_2$ (2050 mL of a 0.08 g/mL stock solution, 627 mmol, 99.999%; Sigma Aldrich Co., St. Louis, Mo.; catalog #202754) at room temperature. Phosphoric acid, $H_3PO_4$ (58.7 mL of an 85 wt %, density=1.684 g/mL, 857 mmol; Acros Organics, Geel, Belgium; catalog #295700010), was added to the slurry, providing a solution containing potassium ($K^+$, $M^I$) and barium ($Ba^{2+}$, $M^{II}$) cations. The final pH of the suspension was about 1.6. The acid-containing suspension was then dried slowly in a glass beaker at 80° C. using a heating plate while magnetically stirring the suspension until the liquid was evaporated and the material was almost completely dried. Heating was continued in a oven with air circulation (G1530A, HP6890 GC; Agilent Corp., Santa Clara, Calif.) at 50° C. for 5.3 h, then at 80° C. for 10 h (0.5° C./min ramp), following by cooling down at 25° C. The material was calcined at 120° C. for 2 hours (0.5° C./min ramp) followed by 450° C. for 4 hours (2° C./min ramp) using the same oven. After calcination, the material was left inside the oven until it cooled down by itself at a temperature below 25° C. before it was taken out of the oven. Finally, the catalyst was ground and sieved to about 100 μm to about 200 μm.

Example 2

113.6 g of an 88 wt % L-lactic acid solution (Purac Corp., Lincolnshire, Ill.) was diluted with 386.4 g of distilled water to provide a solution with an expected lactic acid concentration of 20 wt %. This solution was heated to 95° C.-100° C. and for 12-30 hours. Then, the solution was cooled to room temperature, and its lactic acid and lactic acid oligomers concentrations were measured by HPLC (Agilent 1100 system; Santa Clara, Calif.) equipped with a DAD detector and a Waters Atlantis T3 column (Catalog #186003748; Milford, Mass.) using methods generally known by those having ordinary skill in the art. The solution was essentially free of oligomers.

Example 3

454 g of an 88 wt % L-lactic acid solution (Purac Corp., Lincolnshire, Ill.) was diluted with 1,300 g of water. The diluted solution was heated to 95° C. and held at that temperature with stirring for about 4 to 12 hours. Then, the solution was cooled to room temperature, and its lactic acid and lactic acid oligomers concentrations were measured by HPLC (Agilent 1100 system; Santa Clara, Calif.) equipped with a DAD detector and a Waters Atlantis T3 column (Catalog #186003748; Milford, Mass.) using methods generally known by those having ordinary skill in the art. The solution was essentially free of oligomers. Finally, the solution was further diluted with water to yield a 20 wt % L-lactic acid aqueous solution and essentially free of oligomers.

Example 4

A 13" (33 cm) long stainless steel glass lined tube (SGE Analytical Science Pty Ltd., Ringwood, Australia) with a 4.0 mm internal diameter (ID) was packed with 3" (7.6 cm) bed length glass wool and 5" (12.7 cm) the catalyst from Example 1 (1.6 mL bed volume) to give an 2.55 mL total packed bed (8" or 20.3 cm) and 1.6 mL (5" or 12.7 cm) of free space at the top of the reactor. The tube was placed inside an aluminum block and placed in a clam shell furnace series 3210 (Applied Test Systems, Butler, Pa.), such that the top of the packed bed was aligned with the top of the aluminum block. The reactor was setup in a down flow arrangement and was equipped with a Knauer Smartline 100 feed pump (Berlin, Germany), a Brooks 0254 gas flow controller (Hatfield, Pa.), a Brooks back pressure regulator, and a catch tank. The clam shell furnace was heated, such that the reactor wall temperature was kept constant at about 350° C. during the course of the reaction. The reactor was supplied with separate liquid and gas feeds that were mixed together before reaching the catalyst bed. The gas feed was composed of molecular nitrogen at about 360 psig and at a flow of 45 mL/min. The liquid feed was a 20 wt % aqueous solution of L-lactic acid, prepared as in Example 2, and fed at 0.045 mL/min (LHSV of 1.7 $h^{-1}$), giving a residence time of about 1 s (GHSV of 3,600 $h^{-1}$) at STP conditions. After flowing through the reactor, the gaseous stream was cooled and the liquid was collected in the catch tank over 6 h and 42 min (402 min in total) for analysis by off-line HPLC (Agilent 1100 system; Santa Clara, Calif.) equipped with a DAD detector and a Waters Atlantis T3 column (Catalog #186003748; Milford, Mass.) using methods generally known by those having ordinary skill in the art. The gaseous stream was analyzed on-line by GC (Agilent 7890 system; Santa Clara, Calif.) equipped with a FID detector and Varian CP-Para Bond Q column (Catalog # CP7351; Santa Clara, Calif.). The acrylic acid aqueous solution had 14.8 wt % acrylic acid and 1.5 wt % lactic acid. The acrylic acid yield was 80%, its selectivity was 85%, and the lactic acid conversion was 94%.

Example 5

The reactor consisted of an electric clam shell furnace (Applied Test systems, Butler, Pa.) with an 8" (20.3 cm) heated zone with one temperature controller connected in series to another electric clam shell furnace (Applied Test Systems, Butler, Pa.) with a 16" (40.6 cm) heated zone containing two temperature controllers and a reactor tube. The reactor tube consisted of a 13" (33 cm) borosilicate glass-lined tube (SGE Analytical Science Pty Ltd., Ringwood, Australia)) and a 23" (58.4 cm) borosilicate glass lined tube connected in series using a Swagelok™ tee fitting equipped with an internal thermocouple and having an inside diameter of 9.5 mm. The head of the column was fitted with a ⅛" (3.2 mm) stainless steel nitrogen feed line and a 1/16" (1.6 mm) fused silica lined stainless steel liquid feed supply line connected to a HPLC pump (Smartline 100, Knauer, Berlin, Germany) that was connected to a lactic acid feed tank. The bottom of the reactor was connected to a Teflon-lined catch tank using ⅛" (3.2 mm) fused silica lined stainless steel tubing and Swagelok™ fittings. The reactor column was packed with a plug of glass wool, 13 g of fused quartz, 16" (40.7 cm) with catalyst of Example 1 (47 g and 28.8 mL packed bed volume) and topped with 25 g of fused quartz. The reactor tube was placed in an aluminum block and placed into the reactor from above in a downward flow. The reactor was preheated to 375° C. overnight under 0.25 L/min nitrogen. The nitrogen feed was increased to 0.85 L/min during the experiment. The liquid feed was a 20 wt % aqueous solution of L-lactic acid, prepared as in Example 3, and fed at 0.845 mL/min (LHSV of 1.8 $h^{-1}$; 50.7 g/h), giving a residence time of about 1 s (GHSV of 3,600 $h^{-1}$) at STP conditions. The clam shell heaters were adjusted to give an internal temperature about 350° C. After flowing through the reactor, the gaseous stream was cooled and the liquid was collected in the catch tank for analysis by off-line HPLC using an Agilent 1100 system (Santa Clara, Calif.) equipped with a DAD detector and a Waters Atlantis T3 column (Catalog #186003748; Milford, Mass.) using methods generally known by those having ordinary skill in the art. The gaseous stream was analyzed on-line by GC using an Agilent 7890 system (Santa Clara, Calif.) equipped with a FID detector and Varian CP-Para Bond Q column (Catalog # CP7351; Santa Clara, Calif.). The crude reaction mixture was cooled and collected over 159 h to give 748 g acrylic acid as a crude mixture in 54% yield, 75% acrylic acid selectivity, and 69% conversion of lactic acid. The acrylic acid yield, corrected for the losses during the evaporating step, was 61% and its selectivity was 89%. The acrylic acid aqueous concentration was 8.4 wt %, and that of lactic acid was 6.3 wt %.

Example 6

Experiments without catalyst present further demonstrated the effect of feed stabilization in a quartz reactor. All runs were performed using a 0.2 mL reactor. Empty reactors were compared to those packed with fused silica ($SiO_2$) (Sigma Aldrich Co., St. Louis, Mo.) and Zirblast (Saint Gobain Zirpro, Le Pontet Cedex, France) in both stainless steel (SS) and quartz reactors. The results are reported in Table 1 below.

The 0.2 mL reactor system comprised temperature and mass flow controllers and was supplied with separate liquid and gas feeds that were mixed together before reaching the catalyst bed. The gas feed was composed of molecular nitrogen ($N_2$) and helium (He), which was added as an internal standard for the gas chromatograph (GC) analysis. The liquid feed was a 20 wt % aqueous solution of L-lactic acid, prepared as in 2, and fed to the top of the reactor while controlling the pump pressure to about 360 psig to overcome any pressure drop from the catalyst bed. Quartz or stainless steel reactors with an aspect ratio (i.e., length/diameter) of 75 were used.

Various catalyst beds and gas feed flows were used resulting in a range of space velocities (reported herein). The reactor effluent was also connected to another nitrogen dilution line, which diluted the effluent by a factor of two. The helium internal standard normalized any variation in this dilution for analytical purposes. The condensed products were collected by a liquid sampling system cooled to between 6.5° C. to 10° C. while the gaseous products accumulated on the overhead space of a collection vial. The overhead gaseous products were analyzed using sampling valves and online gas chromatography (GC).

The feed was equilibrated for 1 hour, after which time the liquid sample was collected for 2.7 hours and analyzed at the end of the experiment by offline HPLC. During this time, the gas products were analyzed online twice by GC and reported as an average. Liquid products were analyzed by high performance liquid chromatography (HPLC) using an Agilent 1200 Series instrument (Agilent Technologies, Santa Clara, Calif.), a Supelcogel-H column (4.6×250 mm; Supelco, St. Louis, Mo.), and a diode-array and a refraction index (RI) detectors. Analytes were eluted isocratically, using 0.005 M $H_2SO_4$ (aq.) as the elution buffer, over a period of 30 min and at a flow of 0.2 mL/min. The column and RI detector temperatures were set at 30° C. Gaseous products were analyzed by an Interscience Compact gas chromatography (GC) system (Interscience BV, Breda, Netherlands) using three detectors (one flame ionization detector—FID and two thermal conductivity—TCD—detectors "A" and "B," referred to hereinafter as "TCD-A" and "TCD-B," respectively). The gaseous products were reported as an average given by two sequential GC chromatograms.

The TCD-A column was an Rt-Q Bond (Restek Corp., Bellefonte, Pa.), having 26 m in length and an I.D. of 0.32 mm with a film thickness of 10 μm and using a pre-column of 2 m. The pressure was set to 150 kPa, with a split flow of 10 mL/min. The column oven temperature was set to 100° C. with a vale oven temperature of 50° C. The flow was set to 5.0 mL/min, with a carrier gas of helium. The TCD-B column was a Mol sieve MS5A (Restek Corp., Bellefonte, Pa.), having a length of 21 m and a film thickness of 10 μm and using a pre-column of 2 m. The pressure was set to 200 kPa, with a split flow of 10 mL/min. The column oven temperature was set to 70° C. with a vale oven temperature of 50° C. The flow was set to 2.0 mL/min, with a carrier gas of argon. The FID column was a RTx-624 (Restek, Bellefonte, Pa.), having a length of 28 m and an inner diameter of 0.25 mm with a film thickness of 14 mm and using a pre-column of 2 m. The pressure was set to 100 kPa, with a split flow to 20 mL/min. The column oven temperature was set to 45° C. with a vale oven temperature of 50° C.

VI Results

TABLE 1

| Inert Packing | Reactor Material | GHSV, ($h^{-1}$) | LA Conversion, (%) | AA Selectivity, (%) | AA Yield, (%) | PA Yield, (%) |
|---|---|---|---|---|---|---|
| Empty | Quartz | 3,453 | 18 | 0 | 0.2 | 0.2 |
| Empty | SS | 3,453 | 71.7 | 0 | 0.2 | 13.7 |
| Fused $SiO_2$ | Quartz | 3,489 | 25 | 0.05 | 1.4 | 2.9 |
| Fused $SiO_2$ | SS | 3,489 | 68.6 | 0 | 0 | 13.4 |
| Zirblast | Quartz | 3,489 | 21.8 | 0 | 0 | 0.2 |
| Zirblast | SS | 3,489 | 70 | 0 | 0 | 13 |

The results reported in Table 1 indicate that at high space velocities, very little byproducts were observed when quartz reactors were used, with or without inert packing. Thus, it was determined that the use of quartz reactors minimized two important side reactions: lactic acid oligomerization and reduction to propionic acid. This is important to evaluating the true activity of catalysts.

The foregoing description is given for clearness of understanding only, and no unnecessary limitations should be understood therefrom, as modifications within the scope of the invention may be apparent to those having ordinary skill in the art.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for converting hydroxypropionic acid, hydroxypropionic acid derivatives, or mixtures thereof to acrylic acid, acrylic acid derivatives, or mixtures thereof comprising the following steps:
   a) Providing an aqueous solution comprising hydroxypropionic acid, hydroxypropionic acid derivatives, or mixtures thereof, wherein said hydroxypropionic acid is in monomeric form in said aqueous solution;
   b) Combining said aqueous solution with an inert gas to form an aqueous solution/gas blend;
   c) Evaporating said aqueous solution/gas blend to produce a gaseous mixture; and
   d) Dehydrating said gaseous mixture by contacting said gaseous mixture with a dehydration catalyst under a pressure of at least about 80 psig, producing said acrylic acid, acrylic acid derivatives, or mixtures thereof, wherein said catalyst comprises: (a) at least one condensed phosphate anion selected from the group consisting of formulae (I), (II), and (III), $[P_n O_{3n+1}]^{(n+2)-}$ (I), $[P_n O_{3n}]^{n+}$ (II), $[P_{(2m+n)} O_{(5m+3n)}]^{n-}$ (III), wherein n is at least 2 and m is at least 1, and (b) at least two different cations, wherein said catalyst is essentially neutrally charged, and further wherein the molar ratio of phosphorus to the at least two different cations is between about 0.7 and about 1.7.

2. The process of claim 1, wherein said molar ratio of phosphorus to the at least two different cations is about 1.

3. The process of claim 1, wherein the pressure is from about 80 psig to about 550 psig.

4. The process of claim 1, wherein the pressure is from about 150 psig to about 500 psig.

5. The process of claim 1, wherein the temperature during the evaporating step is from about 165° C. to about 450° C.

6. The process of claim 1, wherein the temperature during the evaporating step is from about 250° C. to about 375° C.

7. The process of claim 1, wherein the GHSV in the evaporating step is from about 720 $h^{-1}$ to about 36,000 $h^{-1}$.

8. The process of claim 1, wherein the temperature during the dehydrating step is from about 150° C. to about 500° C.

9. The process of claim 1, wherein the temperature during the dehydrating step is from about 300° C. to about 450° C.

10. The process of claim 1, wherein the GHSV in the dehydrating step is from about 720 $h^{-1}$ to about 36,000 $h^{-1}$.

11. The process of claim 1, wherein the GHSV in the dehydrating step is about 3,600 $h^{-1}$.

12. The process of claim 1, wherein the hydroxypropionic acid, hydroxypropionic acid derivatives, or mixtures thereof comprise from about 5 wt % to about 50 wt % of said aqueous solution.

13. The process of claim 1, wherein the hydroxypropionic acid, hydroxypropionic acid derivatives, or mixtures thereof comprise from about 10 wt % to about 25 wt % of said aqueous solution.

14. The process of claim 1, wherein the inert gas is selected from the group consisting of air, nitrogen, helium, argon, carbon dioxide, carbon monoxide, steam, and mixtures thereof.

15. The process of claim 1, wherein the gaseous mixture comprises from about 1 mol % to about 10 mol % of said hydroxypropionic acid, hydroxypropionic acid derivatives, or mixtures thereof.

16. The process of claim 1, wherein said evaporating step is performed in a reactor, wherein said reactor has an interior surface comprising material selected from the group consisting of quartz, borosilicate glass, silicon, hastelloy, inconel, manufactured sapphire, stainless steel, and mixtures thereof.

17. The process of claim 1, wherein said dehydrating step is performed in a reactor, wherein said reactor has an interior surface comprising material selected from the group consisting of quartz, borosilicate glass, silicon, hastelloy, inconel, manufactured sapphire, stainless steel, and mixtures thereof.

18. The process of claim 1, wherein said hydroxypropionic acid is lactic acid.

19. The process of claim 18, wherein the acrylic acid selectivity from the lactic acid is at least 50%.

20. The process of claim 18, wherein the acrylic acid selectivity from the lactic acid is at least 80%.

21. The process of claim 18, wherein the propanoic acid selectivity from the lactic acid is less than about 5%.

22. The process of claim 18, wherein the propanoic acid selectivity from the lactic acid is less than about 1%.

23. The process of claim 18, wherein the conversion of said lactic acid is more than about 50%.

24. The process of claim 18, wherein the conversion of said lactic acid is more than about 80%.

25. The process of claim 1, wherein said evaporating step is performed under a pressure of from about 80 psig to about 550 psig.

26. A process for converting hydroxypropionic acid, hydroxypropionic acid derivatives, or mixtures thereof to acrylic acid, acrylic acid derivatives, or mixtures thereof comprising the following steps:
   a) Providing an aqueous solution comprising hydroxypropionic acid, hydroxypropionic acid derivatives, or mixtures thereof, wherein said hydroxypropionic acid comprises oligomers in said aqueous solution;
   b) Heating said aqueous solution at a temperature from about 50° C. to about 100° C. to remove said oligomers of said hydroxypropionic acid and produce an aqueous solution of monomeric hydroxypropionic acid;
   c) Combining said aqueous solution of monomeric hydroxypropionic acid with an inert gas to form an aqueous solution/gas blend;
   d) Evaporating said aqueous solution/gas blend to produce a gaseous mixture; and
   e) Dehydrating said gaseous mixture by contacting said mixture with a dehydration catalyst, producing said acrylic acid, acrylic acid derivatives and mixtures thereof, wherein said catalyst comprises: (a) at least one condensed phosphate anion selected from the group consisting of formulae (I), (II), and (III), $[P_nO_{3n+1}]^{(n+2)-}$ (I), $[P_nO_{3n}]^{n-}$ (II), $[P_{(2m+n)}O_{(5m+3n)}]^{n-}$ (III), wherein n is at least 2 and m is at least 1, and (b) at least two different cations, wherein said catalyst is essentially neutrally charged, and further wherein the molar ratio of phosphorus to the at least two different cations is between about 0.7 and about 1.7.
   f).

27. The process of claim 26, wherein, after said heating step, said oligomers comprise less than about 5 wt % based on the total amount of hydroxypropionic acid, hydroxypropionic acid derivatives, or mixtures thereof.

28. A process for converting hydroxypropionic acid, hydroxypropionic acid derivatives, or mixtures thereof to acrylic acid, acrylic acid derivatives, or mixtures thereof comprising the following steps:
   a) Providing an aqueous solution comprising hydroxypropionic acid, hydroxypropionic acid derivatives, or mixtures thereof, wherein said hydroxypropionic acid is in monomeric form in said aqueous solution;
   b) Combining said aqueous solution with an inert gas to form an aqueous solution/gas blend;
   c) Evaporating said aqueous solution/gas blend to produce a gaseous mixture;
   d) Dehydrating said gaseous mixture by contacting said mixture with a dehydration catalyst, producing said acrylic acid, acrylic acid derivatives, or mixtures thereof, wherein said catalyst comprises: (a) at least one condensed phosphate anion selected from the group consisting of formulae (I), (II), and (III), $[P_nO_{3n+1}]^{(n+2)-}$ (I), $[P_nO_{3n}]^{n-}$ (II), $[P_{(2m+n)}O_{(5m+3n)}]^{n-}$ (III), wherein n is at least 2 and m is at least 1, and (b) at least two different cations, wherein said catalyst is essentially neutrally charged, and further wherein the molar ratio of phosphorus to the at least two different cations is between about 0.7 and about 1.7; and
   e) Cooling said acrylic acid, acrylic acid derivatives, or mixtures thereof at a GHSV of more than about 360 h$^{-1}$.

29. The process of claim 28, wherein the GHSV in the cooling step is more than about 720 h$^{-1}$.

30. A process for converting lactic acid to acrylic acid comprising the following steps:
   a) Diluting an about 88% lactic acid aqueous solution with water to form an about 20 wt % lactic acid aqueous solution;
   b) Heating said about 20 wt % lactic acid aqueous solution at a temperature from about 95° C. to about 100° C. to remove oligomers of said lactic acid, producing a monomeric lactic acid aqueous solution comprising at least 95 wt % of said lactic acid in monomeric form based on the total amount of lactic acid;
   c) Combining said monomeric lactic acid aqueous solution with nitrogen to form an aqueous solution/gas blend;
   d) Evaporating said aqueous solution/gas blend in a reactor with inside surface of borosilicate glass at a GHSV of about 7,200 h$^{-1}$ at a temperature from about 300° C. to about 350° C. to produce a gaseous mixture comprising about 2.5 mol % lactic acid and about 50 mol % water;
   e) Dehydrating said gaseous mixture in a reactor with inside surface of borosilicate glass at a GHSV of about 3,600 h$^{-1}$ at a temperature from about 350° C. to about 425° C. by contacting said mixture with a dehydration catalyst under a pressure of about 360 psig, producing said acrylic acid, wherein said catalyst comprises: (a) at least one condensed phosphate anion selected from the group consisting of formulae (I), (II), and (III), $[P_nO_{3n+1}]^{(n+2)-}$ (I), $[P_nO_{3n}]^{n-}$ (II), $[P_{(2m+n)}O_{(5m+3n)}]^{n-}$ (III), wherein n is at least 2 and m is at least 1, and (b) at least two different cations, wherein said catalyst is essentially neutrally charged, and further wherein the molar ratio of phosphorus to the at least two different cations is between about 0.7 and about 1.7; and
   f) Cooling said acrylic acid to give an acrylic acid solution at a GHSV from about 360 h$^{-1}$ to about 36,000 h$^{-1}$.

31. A process for converting hydroxypropionic acid, derivatives of hydroxypropionic acid, and mixtures thereof to acrylic acid, acrylic acid derivatives, or mixtures thereof comprising the following steps:
   a) Providing an aqueous solution comprising hydroxypropionic acid, hydroxypropionic acid derivatives, or mixtures thereof, wherein said hydroxypropionic acid is in monomeric form in said aqueous solution, and wherein the hydroxypropionic acid, hydroxypropionic acid derivatives, or mixtures thereof comprise from about 10 wt % to about 25 wt % of said aqueous solution;

b) Combining said aqueous solution with an inert gas to form an aqueous solution/gas blend;

c) Evaporating said aqueous solution/gas blend to produce a gaseous mixture; and d) Dehydrating said gaseous mixture by contacting said mixture with a dehydration catalyst producing said acrylic acid, acrylic acid derivatives, or mixtures thereof, wherein said catalyst comprises: (a) at least one condensed phosphate anion selected from the group consisting of formulae (I), (II), and (III), $[P_nO_{3n+1}]^{(n+2)-}$ (I), $[P_nO_{3n}]^{n-}$ (II), $[P_{(2m+n)}O_{(5m+3n)}]^{n-}$ (III), wherein n is at least 2 and m is at least 1, and (b) at least two different cations, wherein said catalyst is essentially neutrally charged, and further wherein the molar ratio of phosphorus to the at least two different cations is between about 0.7 and about 1.7.

32. The process of claim 31, wherein the hydroxypropionic acid, hydroxypropionic acid derivatives, or mixtures thereof comprise about 20 wt % of said aqueous solution.

33. A process for converting alkyl lactates to acrylic acid, acrylic acid derivatives, or mixtures thereof comprising the following steps:

a) Providing alkyl lactates or a solution comprising alkyl lactates and a solvent;

b) Combining said alkyl lactates or said solution comprising said alkyl lactates and said solvent with an inert gas to form a liquid/gas blend;

c) Evaporating said liquid/gas blend to produce a gaseous mixture; and d) Dehydrating said gaseous mixture by contacting said gaseous mixture with a dehydration catalyst under a pressure of at least about 80 psig, producing said acrylic acid, acrylic acid derivatives, or mixtures thereof, wherein said catalyst comprises: (a) at least one condensed phosphate anion selected from the group consisting of formulae (I), (II), and (III), $[P_nO_{3n+1}]^{(n+2)-}$ (I), $[P_nO_{3n}]^{n-}$ (II), $[P_{(2m+n)}O_{(5m+3n)}]^{n-}$ (III), wherein n is at least 2 and m is at least 1, and (b) at least two different cations, wherein said catalyst is essentially neutrally charged, and further wherein the molar ratio of phosphorus to the at least two different cations is between about 0.7 and about 1.7.

34. The process of claim 33, wherein said alkyl lactates are selected from the group consisting of methyl lactate, ethyl lactate, butyl lactate, 2-ethylhexyl lactate, and mixtures thereof.

35. The process of claim 33, wherein the solvent is selected from the group consisting of water, methanol, ethanol, butanol, 2-ethylhexanol, isobutanol, isooctyl alcohol, and mixtures thereof.

* * * * *